United States Patent
Chapman

(10) Patent No.: US 9,580,683 B2
(45) Date of Patent: Feb. 28, 2017

(54) ES CELL CYTOPLASM OR OOPLASM TRANSFER TO REJUVENTATE RECIPIENT CELLS

(71) Applicant: Advanced Cell Technology, Inc., Marlborough, MA (US)

(72) Inventor: Karen B. Chapman, Boston, MA (US)

(73) Assignee: Advanced Cell Technology, Inc., Alameda, CA (US)

( * ) Notice: Subject to any disclaimer, the term of this patent is extended or adjusted under 35 U.S.C. 154(b) by 0 days.

(21) Appl. No.: 14/302,384

(22) Filed: Jun. 11, 2014

(65) Prior Publication Data
US 2015/0132853 A1   May 14, 2015

Related U.S. Application Data

(63) Continuation of application No. 13/617,988, filed on Sep. 14, 2012, now abandoned, which is a continuation of application No. 13/366,518, filed on Feb. 6, 2012, now abandoned, which is a continuation of application No. 10/831,599, filed on Apr. 23, 2004, now abandoned, which is a continuation of application No. 09/736,268, filed on Dec. 15, 2000, now abandoned, which is a continuation-in-part of application No. PCT/US00/18063, filed on Jun. 30, 2000.

(60) Provisional application No. 60/141,250, filed on Jun. 30, 1999.

(51) Int. Cl.
| | | |
|---|---|---|
| C12N 15/00 | (2006.01) | |
| C12N 5/0735 | (2010.01) | |
| A61K 48/00 | (2006.01) | |
| C12N 5/074 | (2010.01) | |
| C12N 5/16 | (2006.01) | |
| C12N 9/12 | (2006.01) | |
| C12N 15/79 | (2006.01) | |
| C12N 15/873 | (2010.01) | |
| C12N 5/071 | (2010.01) | |
| A61K 35/12 | (2015.01) | |

(52) U.S. Cl.
CPC ............ *C12N 5/0606* (2013.01); *A61K 48/00* (2013.01); *C12N 5/0602* (2013.01); *C12N 5/0696* (2013.01); *C12N 5/16* (2013.01); *C12N 9/1241* (2013.01); *C12N 15/79* (2013.01); *C12N 15/873* (2013.01); *A61K 35/12* (2013.01); *C12N 2501/00* (2013.01); *C12N 2503/00* (2013.01); *C12N 2506/00* (2013.01); *C12N 2510/04* (2013.01); *C12N 2517/10* (2013.01)

(58) Field of Classification Search
CPC C12N 15/873; C12N 5/0606; C12N 2510/00; C12N 2517/02; C12N 15/8776; C12N 2502/02; C12N 5/0662; C12N 15/52; C12N 5/0603; C12N 5/0604; C12N 5/0696; C12N 2506/00; C12N 5/16; C12N 2510/04; C12N 2517/10; C12N 2501/60; C12N 2517/04; C12N 9/1241; C12N 15/8202; C12N 15/85; C12N 9/6424

See application file for complete search history.

(56) References Cited

U.S. PATENT DOCUMENTS

| | | |
|---|---|---|
| 5,480,772 A | 1/1996 | Wangh |
| 5,651,992 A | 7/1997 | Wangh |
| 5,830,651 A | 11/1998 | Cauley et al. |
| 6,011,197 A | 1/2000 | Strelchenko et al. |
| 2001/0012513 A1 | 8/2001 | Robl et al. |
| 2002/0001842 A1 | 1/2002 | Chapman |
| 2003/0044976 A1 | 3/2003 | Dominko et al. |
| 2004/0199935 A1 | 10/2004 | Chapman et al. |
| 2013/0104253 A1 | 4/2013 | Chapman et al. |

FOREIGN PATENT DOCUMENTS

| | | |
|---|---|---|
| JP | 63044526 A | 2/1988 |
| JP | 2002-512787 A | 5/2002 |
| WO | WO 97/07669 A2 | 10/1997 |
| WO | WO 97/35967 A2 | 10/1997 |
| WO | WO 98/74841 * | 2/1998 |
| WO | WO 99/05266 A2 | 2/1999 |
| WO | WO 99/55841 A2 | 11/1999 |
| WO | WO 00/65137 A1 | 11/2000 |
| WO | WO 01/46401 A1 | 6/2001 |

OTHER PUBLICATIONS

Database WPI, Section Ch, Week 198814. Derwent Abstract. Derwent Publications Ltd. London, GB. Feb. 28, 2005. 2 Pages.
Bain et al., Embryonic stem cells express neuronal properties in vitro. Dev Biol. 1995;168:342-357.

(Continued)

*Primary Examiner* — Deborah Crouch
(74) *Attorney, Agent, or Firm* — DLA Piper LLP (US)

(57) ABSTRACT

Methods for de-differentiating or altering the life-span of desired "recipient" cells, e.g., human somatic cells, by the introduction of cytoplasm from a more primitive, less differentiated cell type, e.g., oocyte or blastomere are provided. These methods can be used to produce embryonic stem cells and to increase the efficiency of gene therapy by allowing for desired cells to be subjected to multiple genetic modifications without becoming senescent. Such cytoplasm may be fractionated and/or subjected to subtractive hybridization and the active materials (sufficient for de-differentiation) identified and produced by recombinant methods.

31 Claims, No Drawings

(56) References Cited

OTHER PUBLICATIONS

Bodnar et al., Extension of life-span by introduction of telomerase into normal human cells. Science. Jan. 16, 1998;279(5349):349-52.
Campbell, Nuclear equivalence, nuclear transfer, and the cell cycle. Cloning. 1999;1(1):3-15.
Cibelli et al., Cloned transgenic calves produced from nonquiescent fetal fibroblasts. Science. May 22, 1998;280(5367):1256-8.
Cohen et al., Ooplasmic transfer in mature human oocytes. Mol Hum Reprod. Mar. 1998;4(3):269-80.
Collas., Cytoplasmic control of nuclear assembly. Reprod Fertil Dev. 1998;10:581-92.
Dimitrov et al., Remodeling somatic nuclei in Xenopus laevis egg extracts: molecular mechanisms for the selective release of histones H1 and H1(0) from chromatin and the acquisition of transcriptional competence. EMBO J; 1996:15:5897-5906.
Do et al. Nuclei of Embryonic Stem Cells Reprogram Somatic Cells. Stem Cells. 2004;22: 941-49.
Dominko et al., Bovine oocyte cytoplasm supports development of embryos produced by nuclear transfer of somatic cell nuclei from various mammalian species. Biol Reprod. 1999;60:1496-1502.
Fricker et al., Site-specific migration and neuronal differentiation of human neural progenitor cells after transplantation in the adult rat brain. J Neurosci. 1999;19:5990-6005.
Hansis et al., Nuclear reprogramming of human somatic cells by xenopus egg extract requires BRG1. 2004. Curr Biol. 2004;14:1475-80.
Katagiri et al., Remodeling of sperm chromatin induced in egg extracts of amphibians. Int J Dev Biol. 1994;38:209-16.
Kato et al., Eight calves cloned from somatic cells of a single adult. Science. Dec. 11, 1998;282(5396):2095-8.
Lanzendorf et aL, Pregnancy following transfer of ooplasm from cryopreserved thawed donor oocytes into recipient oocytes. Fertility and Sterility. 1999;71:575-77.
Lewitzky et al., Reprogramming somatic cells towards pluripotency by defined factors. Curr Opin Biotechnol. Oct. 2007;18(5):467-73.
Li et al., Nuclear transfer: progress and quandaries. Reprod Biol Endocrinol. Nov. 7, 2003;1:84.
Matveeva et al., In vitro and in vivo study of pluripotency in intraspecific hybrid cells obtained by fusion of murine embryonic stem cells with splenocytes. Mol Reprod Dev. Jun. 1998;50(2):128-38.
Maxson et al., Differential stimulation of sea urchin early and late H2B histone gene expression by a gastrula nuclear extract after injection into Xenopus laevis oocytes. Mol Cell Biol. 1988;8:1236-46.
Meirelles et al., Complete replacement of the mitochondrial genotype in a Bos indicus calf reconstructed by nuclear transfer to a Bos taurus oocyte. Genetics. May 2001;158(1):351-6.
Mitalipov et al., Rhesus monkey embryos produced by nuclear transfer from embryonic blastomeres or somatic cells. Biol Reprod. May 2002;66(5):1367-73.
Nakagawa et al., Generation of induced pluripotent stem cells without Myc from mouse and human fibroblasts. Nat Biotechnol. Jan. 2008;26(1):101-6. Epub Nov. 30, 2007.
Prather et al., Nuclear transplantation in Early Pig Embryos. Bio Reprod. 1989;41:414-418.
Simerly et al., Molecular correlates of primate nuclear transfer failures. Science. Apr. 11, 2003;300(5617):297.
Smith et al., Cytoplasmic transfer of the mitogenic response to platelet-derived growth factor. Proc Nat'l Acad Sci USA. 1981;78:4363-7.
Tada et al., Embryonic germ cells induce epigenetic reprogramming of somatic nucleus in hybrid cells. EMBO J. Nov. 3, 1997;16(21):6510-20.
Takahashi et al., Induction of pluripotent stem cells from adult human fibroblasts by defined factors. Cell. Nov. 30, 2007;131(5):861-72.
Taranger et al., Induction of dedifferentiation, genomewide transcriptional programming, and epigenetic reprogramming by extracts of carcinoma and embryonic stem cells. Mol Biol Cell. Dec. 2005;16(12):5719-35.
Thomson., Embryonic stem cell lines derived from human blastocysts. Science. 1998;282:1145-7.
Wangh et al., Efficient reactivation of Xenopus erythrocyte nuclei in Xenopus egg extracts. J Cell Sci. 1995;108:2187-96.
Weisz et al., Allogenic fetal retinal pigment epithelial cell transplant in a patient with geographic atrophy, Retina. 1999;19(6):540-5.
Westphal et al., A Signaling Complex of Ca2+-Calmodulin-Dependent Portein Kinase IV and Protein Phosphatase 2A, Science May 22, 1998;280 (5367):1258-1261.
Willadsen, Nuclear transplantation in sheep embryos. Nature. 1986;320:63-5.
Wilmut et al., Viable offspring derived from fetal and adult mammalian cells. Nature. 1997;385:810-13.
Ziegler, Phenotypic expression of malignancy in hybrid and cybrid mouse cells. Somatic Cells Genetics. 1978;4:477-89.

\* cited by examiner

ES CELL CYTOPLASM OR OOPLASM TRANSFER TO REJUVENATE RECIPIENT CELLS

CROSS REFERENCE TO RELATED APPLICATIONS

This application is a continuation of U.S. patent application Ser. No. 13/617,988 filed Sep. 14, 2012, currently pending, which is a continuation of U.S. patent application Ser. No. 13/366,518 filed Feb. 6, 2012, abandoned, which is a continuation of U.S. patent application Ser. No. 10/831,599 filed Apr. 23, 2004, abandoned, which is a continuation of U.S. patent application Ser. No. 09/736,268 filed Dec. 15, 2000, abandoned, which is a continuation-in-part of International Patent Application No. PCT/US00/18063, filed Jun. 30, 2000, which claims priority from U.S. Provisional Application Ser. No. 60/141,250, filed Jun. 30, 1999, the entire contents of each of which are incorporated herein by reference.

FIELD OF THE INVENTION

The present invention relates to methods for "de-differentiating" and/or altering the life-span of desired recipient cells, preferably human somatic cells. These methods have application especially in the context of cell therapies and the production of genetically modified cells.

BACKGROUND OF THE INVENTION

Nuclear transfer first gained acceptance in the 1960's with amphibian nuclear transplantation. (Diberardino, M. A. 1980, "Genetic stability and modulation of metazoan nuclei transplanted into eggs and ooctyes", *Differentiation*, 17-17-30; Diberardino, M. A., N. J. Hoffner and L. D. Etkin, 1984; "Activation of dormant genes in specialized cells", *Science*, 224:946-952; Prather, R. S. and Robl, J. M., 1991, "Cloning by nuclear transfer and splitting in laboratory and domestic animal embryos", In: *Animal Applications of Research in Mammalian Development*, R. A. Pederson, A. McLaren and N. First (ed.), Cold Spring Harbor Laboratory Press.) Nuclear transfer was initially conducted in amphibians in part because of the relatively large size of the amphibian oocyte relative to that of mammals. The results of these experiments indicated to those skilled in the art that the degree of differentiation of the donor nucleus was greatly instrumental, if not determinative, as to whether a recipient oocyte containing such cell or nucleus could effectively reprogram said nucleus and produce a viable embryo. (Diberardino, M. A., N. J. Hoffner and L. D. Etkin, 1984, "Activation of dormant genes in specialized cells.", *Science*, 224:946-952; Prather, R. S. and Robl, J. M., 1991, "Cloning by nuclear transfer and splitting in laboratory and domestic animal embryos", In: *Animal Applications of Research in Mammalian Development*, R. A. Pederson, A. McLaren and N. First (ed.), Cold Spring Harbor Laboratory Press).

Much later, in the mid 1980s, after microsurgical techniques had been perfected, researchers investigated whether nuclear transfer could be extrapolated to mammals. The first procedures for cloning cattle were reported by Robl et al (Robl, J. M., R. Prather, F. Barnes, W. Eyestone, D. Northey, B. Gilligan and N. L. First, 987, "Nuclear transplantation in bovine embryos", *J. Anim. Sci.*, 64:642-647). In fact, Dr. Robl's lab was the first to clone a rabbit by nuclear transfer using donor nuclei from earlier embryonic cells (Stice, S. L. and Robl, J. M., 1988, "Nuclear reprogramming in nuclear transplant rabbit embryos", *Biol. Reprod.*, 39:657-664). Also, using similar techniques, bovines (Prather, R. S., F. L. Barnes, M. L. Sims, Robl, J. M., W. H. Eyestone and N. L. First, 1987, "Nuclear transplantation in the bovine embryo: assessment of donor nuclei and recipient oocyte", *Biol. Reprod.*, 37:859-866) and sheep (Willadsen, S. M., 1986, "Nuclear transplantation in sheep embryos", *Nature*, (Lond) 320:63-65), and putatively porcines (Prather, R. S., M. M. Sims and N. L. First, 1989, "Nuclear transplantation in pig embryos", *Biol. Reprod.*, 41:414), were cloned by the transplantation of the cell or nucleus of very early embryos into enucleated oocytes.

In the early 1990s, the possibility of producing nuclear transfer embryos with donor nuclei obtained from progressively more differentiated cells was investigated. The initial results of these experiments suggested that when an embryo progresses to the blastocyst stage (the embryonic stage where the first two distinct cell lineages appear) that the efficiency of nuclear transfer decreases dramatically (Collas, P. and J. M. Robl, 1991, "Relationship between nuclear remodeling and development in nuclear transplant rabbit embryos", *Biol. Reprod.*, 45:455-465). For example, it was found that trophectodermal cells (the cells that form the placenta) did not support development of the nuclear fusion to the blastocyst stage. (Collas, P. and J. M. Robl, 1991, "Relationship between nuclear remodeling and development in nuclear transplant rabbit embryos", *Biol. Reprod.*, 45:455-465). By contrast, inner cell mass cells (cells which form both somatic and germ line cells) were found to support a low rate of development to the blastocyst stage with some offspring obtained. (Collas P, Barnes F L, "Nuclear transplantation by microinjection of inner cell mass and granulosa cell nuclei", *Mol Reprod Devel.*, 1994, 38:264-267) Moreover, further work suggested that inner cell mass cells which were cultured for a short period of time could support the development to term. (Sims M, First N L, "Production of calves by transfer of nuclei from cultured inner cell mass cells", *Proc Natl Acad Sci*, 1994, 91:6143-6147)

Based on these results, it was the overwhelming opinion of those skilled in the art at that time that observations made with amphibian nuclear transfer experiments would likely be observed in mammals. That is to say, it was widely regarded by researchers working in the area of cloning in the early 1990's that once a cell becomes committed to a particular somatic cell lineage that its nucleus irreversibly loses its ability to become "reprogrammed", i.e., to support full term development when used as a nuclear donor for nuclear transfer. While the exact molecular explanation for the apparent inability of somatic cells to be effectively reprogrammed was unknown, it was hypothesized to be the result of changes in DNA methylation, histone acetylation and factors controlling transitions in chromatin structure that occur during cell differentiation. Moreover, it was believed that these cellular changes could not be reversed.

Therefore, it was quite astounding that in 1998, the Roslin Institute reported that cells committed to somatic cell lineage could support embryo development when used as nuclear transfer donors. Equally astounding, and more commercially significant, the production of transgenic cattle which were produced by nuclear transfer using transgenic fibroblast donor cells was reported shortly thereafter by scientists working at the University of Massachusetts and Advanced Cell Technology.

Also, recently two calves were reportedly produced at the Ishikawa Prefecture Livestock Research Centre in Japan from oviduct cells collected from a cow at slaughter. (Hadfield, P. and A.

Coghlan, "Premature birth repeats the Dolly mixture", *New Scientist*, Jul. 11, 1998) Further, Jean-Paul Renard from INRA in France reported the production of a calf using muscle cells from a fetus. (MacKenzie, D. and P. Cohen, 1998, "A French calf answers some of the questions about cloning", *New Scientist*, March 21). Also, David Wells from New Zealand reported the production of a calf using fibroblast donor cells obtained from an adult cow. (Wells, D. N., 1998, "Cloning symposium: Reprogramming Cell Fate—Transgenesis and Cloning," Monash Medical Center, Melbourne, Australia, April 15-16)

Differentiated cells have also reportedly been successfully used as nuclear transfer donors to produce cloned mice. (Wakayama T, Perry ACF, Zucconi M, Johnsoal K R, Yanagimachi R., "Full-term development of mice from enucleated oocytes injected with cumulus cell nuclei", *Nature*, 1998, 394:369-374).

Still further, an experiment by researchers at the University of Massachusetts and Advanced Cell Technology was recently reported in a lead story in the New York Times, January 1999, wherein a nuclear transfer fusion embryo was produced by the insertion of an adult differentiated cell (cell obtained from the cheek of an adult human donor) into an enucleated bovine oocyte. Thus, it would appear, based on these results, that at least under some conditions differentiated cells can be reprogrammed or de-differentiated.

Related thereto, it was also recently reported in the popular press that cytoplasm transferred from oocyte of a young female donor "rejuvenated" an oocyte of an older woman, such that it was competent for reproduction.

However, it would be beneficial if methods could be developed for converting differentiated cells to embryonic cell types, without the need for cloning, and the production of embryos, especially given their potential for use in nuclear transfer and for producing different differentiated cell types for therapeutic use. Also, it would be beneficial if the cellular materials responsible for de-differentiation and reprogramming of differentiated cells could be identified and produced by recombinant methods, thereby improving the efficiency of cellular reprogramming.

OBJECTS OF THE INVENTION

Therefore, it is an object of the invention to provide novel methods for "de-differentiating" and/or altering the life-span of desired cells.

It is a more specific object of the invention to provide a novel method for "de-differentiating" and/or altering the life-span of a desired differentiated cell by introducing the cell or cell nucleus with cytoplasm and then transplanting the de-differentiated nucleus into a surrogate cytoplast such as from an ES cell of a less differentiated cell, preferably an oocyte or blastomere, or another embryonic cell type.

It is another object of the invention to alter the life-span and/or to de-differentiate desired cells, typically mammalian differentiated cells, prior, concurrent, or subsequent to genetic modification.

It is another object of the invention to provide an improved method of cell therapy wherein the improvement comprises administering cells which have been de-differentiated or have an altered life-span by the introduction of cytoplasm obtained from a cell of a less or undifferentiated state, preferably an oocyte or blastomere or placing nuclei from said somatic cell into a solution containing an extract of the oocyte or blastomere embryo, or ES cell or purified proteins from the same.

It is still another object of the invention to identify the component or components in oocyte cytoplasm responsible for de-differentiation and/or alteration of cell life-span, e.g., by fractionation or subtractive hybridization, i.e. fractionation of protein, RNA or DNA.

It is still another object of the invention to provide a novel method of therapy, especially of the skin, by administering a therapeutically effective amount of cytoplasm obtained from a substantially undifferentiated or undifferentiated cell, preferably an oocyte or blastomere, or the purified active components of the same.

It is another object of the invention to provide novel compositions for therapeutic, dermatologic and/or cosmetic usage that contain cytoplasm derived from substantially undifferentiated or undifferentiated cells, preferably an oocyte or blastomere, or purified active components of same.

It is another object of the invention to provide cells for use in cell therapy which have been "de-differentiated" or have an altered life-span by the introduction of cytoplasm from a substantially undifferentiated or undifferentiated cell, preferably an oocyte or blastomere, or purified active components of same.

It is still another object of the invention to provide an improved method of cloning via nuclear transfer wherein the improvement comprises using as the donor cell or nucleus a cell which has been de-differentiated and/or has had its life-span altered by the introduction of cytoplasm from a substantially undifferentiated or undifferentiated cell, or purified active components of same, or cross-species NT where the purified active component is expressed to facilitate reprogramming.

It is another object of the invention to rejuvenate nuclei isolated from desired differentiated cells by contacting same with cytoplasm from oocytes, blastomeres, ES, or other embryonic cell types.

It is another object of the invention to provide screening assays to identify proteins, or nucleic acid sequences that are released from differentiated cell nuclei upon contacting with cytoplasm, or fractions derived from oocyte cytoplasm from oocytes, blastomeres, ES cells or other embryonic cell types, that are involved in all reprogramming.

It is another specific object of the invention to provide screening assays, e.g. differential or subtractive hybridization to identify mRNAs that expressed in oocyte cytoplasm or in embryonic cell types that are involved in cell programming.

BRIEF DESCRIPTION OF THE INVENTION

The present invention provides novel methods for producing cells, preferably mammalian cells and, most preferably, human cells that have been de-differentiated and/or which have an altered (increased) life-span by the juxtaposition of the donor cell with cytoplasm from an undifferentiated or substantially undifferentiated cell, preferably an oocyte or blastomere, or another embryonic cell type. In a particularly preferred embodiment, the present invention will be used to produce cells in a more primitive state, especially embryonic stem cells or inner cell mass cells.

The resultant cells are useful in gene and cell therapies, and as donor cells or nuclei for use in nuclear transfer.

DEFINITIONS

"Ooctye"—In the present invention, this refers to any oocyte, preferably a mammalian oocyte, that develops from an oogonium and, following meiosis, becomes a mature ovum.

"Metaphase II oocyte"—The preferred stage of maturation of oocytes used for nuclear transfer (First and Prather, Differentiation, 48:1-8). At this stage, the oocyte is sufficiently "prepared" to treat an introduced donor cell or nucleus as it does a fertilizing sperm.

"Donor Cell"—In the present invention, this refers to a cell wherein some or all of its cytoplasm is transferred to another cell ("recipient cell"). The donor cell is typically a primitive or embryonic cell type, preferably an oocyte, blastomere, or inner cell mass cell.

"Recipient Cell"—This refers to a cell into which all or part of the cytoplasm of a donor cell, wherein such donor cell is of a more primitive cell type relative to the recipient cell, is transferred. This transfer can be accomplished by different methods, e.g., microinjection or by contacting donor cells with liposomal encapsulated cytoplasm or enucleating the donor cell and incubating with cytoplasmic extract. Typically, the donor cell is an oocyte, blastomere or inner cell mass cell, and the recipient cell is a somatic cell, preferably a human somatic cell.

"Blastomere"—Embryonic, substantially undifferentiated cells contained in blastocyst stage embryos.

"Embryonic cell or embryonic cell type"—In the present invention, this will refer to any cell, e.g., oocyte, blastomere, embryonic stem cell, inner cell mass cell, or primordial germ cell, wherein the introduction of cytoplasm therefrom into a differentiated cell, e.g., human somatic cell in tissue culture, results in de-differentiation and/or lengthening of the life-span of such differentiated cell.

"Cell having altered life-span"—In the present invention this refers to the change in cell life-span (lengthening) that results when cytoplasm of a more primitive or less differentiated cell type, e.g., an embryonic cell or embryonic cell type, e.g., oocyte or blastomere, is introduced into a desired differentiated cell, e.g., a cultured human somatic cell.

"Embryonic stem cell (ES cell)"—In the present invention this refers to an undifferentiated cell that has the potential to develop into an entire organism, i.e., a cell that is able to propagate indefinitely, maintaining its undifferentiated state and, when induced to differentiate, be capable of giving rise to any cell type of the body. "Nuclear Transfer"—Introduction of cell or nuclear DNA of donor cell into enucleated oocyte which cell or nucleus and oocyte are then fused to produce a nuclear transfer fusion or nucleus fusion embryo. This NT fusion may be used to produce a cloned embryo or offspring or to produce ES cells.

"Telomerase"—A ribonucleoprotein (RNP) particle and polymerase that uses a portion of its internal RNA moiety as a template for telomere repeat DNA synthesis (U.S. Pat. No. 5,583,016; Yu et al, *Nature,* 344:126 (1990); Singer and Gottschling, *Science,* 266:404 (1004); Autexier and Greider, *Genes Develop.,* 8:563 (1994); Gilley et al, *Genes Develop.,* 9:2214 (1995); McEachern and Blackburn, *Nature,* 367:403 (1995); Blackburn, *Ann. Rev. Biochem.,* 61:113 (1992); Greider, *Ann Rev. Biochem.,* 65:337 (1996).) The activity of this enzyme depends upon both its RNA and protein components to circumvent the problems presented by end replication by using RNA (i.e., as opposed to DNA) to template the synthesis of telomeric DNA. Telomerases extend the G strand of telomeric DNA. A combination of factors, including telomerase processivity, frequency of action at individual telomeres, and the rate of degradation of telomeric DNA, contribute to the size of the telomeres (i.e., whether they are lengthened, shortened, or maintained at a certain size). In vitro telomerases may be extremely processive, with the Tetrahymena telomerase adding an average of approximately 500 bases to the G strand primer before dissociation of the enzyme (Greider, *Mol. Cell. Biol.,* 114572 (1991).)

"Genetically modified or altered"—In the present invention this refers to cells that contain one or more modifications in their genomic DNA, e.g., additions, substitutions and/or deletions.

"De-differentiation"—In the present invention, this refers to the changes in a differentiated cell, e.g., human somatic cell in tissue culture, that result upon introduction of cytoplasm from a more primitive, less differentiated cell type, e.g., an oocyte or other embryonic cell.

"Totipotent"—In the present invention this refers to a cell that gives rise to all of the cells in a developing body, such as an embryo, fetus, an animal. The term "totipotent" can also refer to a cell that gives rise to all of the cells in an animal. A totipotent cell can give rise to all of the cells of a developing cell mass when it is utilized in a procedure for creating an embryo from one or more nuclear transfer steps. An animal may be an animal that functions ex utero. An animal can exist, for example, as a live born animal. Totipotent cells may also be used to generate incomplete animals such as those useful for organ harvesting, e.g., having genetic modifications to eliminate growth of a head such as by manipulation of a homeotic gene.

"Ungulate"—In the present invention this refers to a four-legged animal having hooves. In other preferred embodiments, the ungulate is selected from the group consisting of domestic or wild representatives of bovids, ovids, cervids, suids, equids, and camelids. Examples of such representatives are cows or bulls, bison, buffalo, sheep, big-horn sheep, horses, ponies, donkeys, mule, deer, elk, caribou, goat, water buffalo, camels, llama, alpaca, and pigs. Especially preferred in the bovine species are *Bos Taurus, Bos Indicus,* and *Bos buffaloes* cows or bulls.

"Immortalized" or "permanent"—These terms as used in the present invention in reference to cells can refer to cells that have exceeded the Hayflick limit. The Hayflick limit can be defined as the number of cell divisions that occur before a cell line becomes senescent. Hayflick set this limit to approximately 60 divisions for most non-immortalized cells. See, e.g., Hayflick and Moorhead, 1971, Exp. *Cell. Res.,* 25:585-621; and Hayflick, 1965, Exp. *Cell Research,* 37:614-636, incorporated herein by reference in their entireties, including all figures, tables and drawings. Therefore, an immortalized cell line can be distinguished from non-immortalized cell lines if the cells in the cell line are able to undergo more than 60 divisions. If the cells of a cell line are able to undergo more than 60 cell divisions, the cell line is an immortalized or permanent cell line. The immortalized cells of the invention are preferably able to undergo more than 70 divisions, are more preferably able to undergo more than 90 divisions, and are most preferably able to undergo more than 90 cell divisions.

Typically, immortalized or permanent cells can be distinguished from non-immortalized and non-permanent cells on the basis that immortalized and permanent cells can be passaged at densities lower than those of non-immortalized cells. Specifically, immortalized cells can be grown to confluence (e.g., when a cell monolayer spreads across an entire plate) when plating conditions do not allow physical contact between the cells. Hence, immortalized cells can be distinguished from non-immortalized cells when cells are plated at cell densities where the cells do not physically contact one another.

"Culture"—In the present invention this term refers to one or more cells that are static or undergoing cell division in a liquid medium. Nearly any type of cell can be placed in cell culture conditions. Cells may be cultured in suspension and/or in monolayers with one or more substantially similar cells. Cells may be cultured in suspension and/or in monolayers with heterogeneous population cells. The term heterogeneous as utilized in the previous sentence can relate to any cell characteristics, such as cell type and cell cycle stage, for example. Cells may be cultured in suspension and/or in monolayers with feeder cells.

"Feeder Cells"—This refers to cells grown in co-culture with other cells. Feeder cells include, e.g., fibroblasts, fetal cells, oviductal cells, and may provide a source of peptides, polypeptides, electrical signals, organic molecules (e.g., steroids), nucleic acid molecules, growth factors, cytokines, and metabolic nutrients to cells co-cultured therewith. Some cells require feeder cells to be grown in tissue culture.

"Reprogram"—This term as used in the present invention refers to materials and methods that can convert a differentiated cell into a less differentiated, more primitive cell type, e.g., an embryonic stem cell.

"Embryo"—In the present invention this refers to a developing cell mass that has not implanted into the uterine membrane of a maternal host. Hence, the term "embryo" as used herein can refer to a fertilized oocyte, a cybrid (defined herein), a pre-blastocyst stage developing cell mass, and/or any other developing cell mass that is at a stage of development prior to implantation into the uterine membrane of a maternal host. Embryos of the invention may not display a genital ridge. Hence, an "embryonic cell" is isolated from and/or has arisen from an embryo.

"Fetus"—In the present invention refers to a developing cell mass that has implanted into the uterine membrane of a maternal host. A fetus can include such defining features as a genital ridge, for example. A genital ridge is a feature easily identified, by a person of ordinary skill in the art and is a recognizable feature in fetuses of most animal species.

"Fetal cell"—as used herein can refer to any cell isolated from and/or has arisen from a fetus or derived from a fetus.

"Non-fetal cell"—refers to a cell that is not derived or isolated from a fetus.

"Senescence"—In the present invention this refers to the characteristic slowing of growth of non-immortal somatic cells in tissue culture after cells have been maintained in culture for a prolonged period. Non-immortal cells characteristically have a defined life-span before they become senescent and die. The present invention alleviates or prevents senescence by the introduction of cytoplasm from a donor cell, typically an oocyte or blastomere, into a recipient cell, e.g., a cultured human somatic cell.

DETAILED DESCRIPTION OF THE INVENTION

As explained above, the present invention provides novel methods for de-differentiating and/or altering the life-span of desired cells, preferably mammalian cells and, most preferably, human or other primate cells by the introduction of cytoplasm from a more primitive cell type, typically an undifferentiated or substantially undifferentiated cell, e.g., an oocyte or blastomere.

As noted previously, it was recently reported in the popular press that a group working in the area of artificial insemination and infertility successfully transferred the cytoplasm from the oocyte of a younger woman into that of an older woman and thereby rejuvenated the ability of the older oocyte to be competent for fertilization and embryo development. Based on this anecdotal evidence, coupled with recent papers in the scientific literature which suggest that differentiated adult cells may be effectively "reprogrammed" by nuclear transfer, it was theorized that differentiated cells could be effectively "reprogrammed" or "de-differentiated" and/or have their life-span altered (increased) by the introduction of cytoplasm from that of undifferentiated or substantially undifferentiated cell, e.g., an oocyte or blastomere or another embryonic cell type.

While it is presently unknown how the cytoplasm of one cell affects the life-span or state of differentiation of another, it is theorized that the cytoplasm of cells in early or primitive states of development contains one or more substances, e.g., transcription factors and/or other substances that act to trigger or promote cell differentiation. For example, one substance likely contained therein that affects the state of cell differentiation is telomerase. Another substance is OCT-4 and REX. However, Applicant does not wish to be bound to this theory as it is not necessary for an understanding of the invention.

In the present invention, a recipient cell will typically be dedifferentiated in vitro by the introduction of an effective amount of cytoplasm from a donor cell, i.e., an undifferentiated or substantially undifferentiated cell, e.g., an oocyte or blastomere. This introduction or transfer of cytoplasm can be effected by different methods, e.g., by microinjection or by use of a liposomal delivery system. A preferred means comprises the introduction of cytoplasm blebs derived from ES cells, oocytes or other embryonic cells into desired differentiated cells, e.g. mammalian or other cells which are at or near senescence. For example, such cytoplasm blebs can be introduced into genetically modified mammalian cells in order to rejuvenate such cells, e.g. prior to their usage for cell therapy.

Alternatively, cytoplasmic blebs can be contacted with nuclei from differentiated cells to induce rejuvenation.

The recipient cell can be of any species and may be heterologous to the donor cell, e.g., amphibian, mammalian, avian, with mammalian cells being preferred. Especially preferred recipient cells include human and other primate cells, e.g., chimpanzee, cynomolgus monkey, baboon, other Old World monkey cells, caprine, equine, porcine, ovine, and other ungulates, murine, canine, feline, and other mammalian species.

Also, the recipient cell can be any differentiated cell type. Suitable examples thereof include epithelial cells, endothelial cells, fibroblasts, keratinocytes, melanocytes and other skin cell types, muscle cells, bone cells, immune cells such as T and B-lymphocytes, oligodendrocytes, dendritic cells, erythrocytes and other blood cells; pancreatic cells, neural and nerve cell types, stomach, intestinal, esophageal, lung, liver, spleen, kidney, bladder, cardiac, thymus, corneal, and other ocular cell types, etc. In general, the methods have application in any application wherein a source of cells that are in a less differentiated state would be desirable.

As noted, the transferred cytoplasm will be obtained from a "donor" cell that is in a less differentiated state or more primitive state than the recipient cell. Typically, the cytoplasm will be derived from oocytes or cells of early stage embryos, e.g., blastomeres or inner cell mass cells derived from early stage embryos. In general, it is preferred that the donor cytoplasm be obtained from oocytes or other embryonic cells that are in an undifferentiated or substantially undifferentiated state. Bovine oocytes are a preferred source because they can be readily obtained in large quantities from slaughterhouses.

Recently there have been reports in the literature concerning the production of cultures comprising embryonic stem cells that reportedly express or do not express certain markers characteristic of embryonic stem cells. It is therefore also preferable that donor cytoplasm be obtained from an oocyte or other cell that expresses or does not express cell markers which are characteristic of an undifferentiated, embryonic cell type. Such markers on primate ES cells include, by way of example, SSEA-1 (−); SSEA-3 (+); SSEA-4 (+); TRA-1-60 (+); TRA-1-81 (+); and alkaline phosphatase (+). (See U.S. Pat. No. 5,843,780 to Thomson, issued Dec. 1, 1998).

As discussed above, it is also desirable that telomerase and/or a DNA sequence or other compound that provides for the expression of telomerase be introduced into the recipient cell, e.g., a mammalian cell and, more preferably, a human or non-human primate cell. The isolation of telomerase and cloning of the corresponding DNA has been reported prior to the present invention. For example, WO 98/14593, published Apr. 9, 1998, by Cech et al, reports telomerase nucleic acid sequences derived from *Eeuplotes aediculatus, Saccharomyces, Schizosaccharomyces*, and human, as well as polypeptides comprising telomerase protein subunits. Also, WO 98/14592, to Cech et al, published Apr. 9, 1998, discloses compositions containing human telomerase reverse transcriptase, the catalytic protein subunit of human telomerase. Also, U.S. Pat. Nos. 5,837,857 and 5,583,414 describe nucleic acids encoding mammalian telomerases.

Still further, U.S. Pat. No. 5,830,644, issued to West et al; U.S. Pat. No. 5,834,193, issued to Kzolowski et al, and U.S. Pat. No. 5,837,453, issued to Harley et al, describe assays for measuring telomerase length and telomerase activity and agents that affect telomerase activity. These patents and PCT applications are incorporated by reference in their entirety herein.

Thus, in the present invention, desired cells, e.g., cultured human somatic cells, may be de-differentiated or reprogrammed in tissue culture by the introduction of cytoplasm of a more primitive cell type, e.g., an oocyte or embryonic cell type alone or in conjunction with telomerase. The introduction of cytoplasm from a donor oocyte or embryonic cell, e.g., blastomere, may be accomplished by various methods. For example, this can be effected by microsurgically removing part or all of the cytoplasm of a donor oocyte or blastomere or other embryonic cell type with a micropipette and microinjecting such cytoplasm into that of a recipient mammalian cell. It may also be desirable to remove cytoplasm from the recipient cell prior to such introduction. Such removal may be accomplished by well known microsurgical methods. Alternatively, the cytoplasm and/or telomerase or telomerase DNA can be introduced using a liposomal delivery system.

The present methods should provide a means of producing embryonic stem cells, e.g., mammalian embryonic stem cells, and most desirably, human embryonic stem cells, by reprogramming or de-differentiating desired cells in tissue culture. These cells are desirable from a therapeutic standpoint since such cells can be used to give rise to any differentiated cell type. The resultant differentiated cell types may be used in cell transplantation therapies.

Another significant application of the present invention is for gene therapy. To date, many different genes of significant therapeutic importance have been identified and cloned. Moreover, methods for stably introducing such DNAs into desired cells, e.g., mammalian cells and, more preferably, human somatic cell types, are well known. Also, methods for effecting site-specific insertion of desired DNAs via homologous recombination are well known in the art.

However, while suitable vectors and methods for introduction and detection of specific DNAs into desired somatic cells are known, a significant obstacle to the efficacy of such methods is the limited life-span of normal, i.e., non-immortal cells, in tissue culture. This is particularly problematic in situations wherein the introduction of multiple DNA modifications, e.g., deletions, substitutions, and/or additions is desired. Essentially, while methods for effecting targeted DNA modifications are known, the requisite time to effect and select for such modifications can be very lengthy. Thus, the cells may become senescent or die before the desired DNA modifications have been effected.

The present invention will alleviate this inherent constraint of gene and cell therapy by introducing the cytoplasm of an oocyte or other embryonic cell type into recipient cells prior, concurrent or subsequent to genetic modification. The introduction of such cytoplasm alone or in combination with telomerase or a DNA or another compound that results in the expression of telomerase, will reprogram the genetically modified cell and enable it to have a longer life-span in tissue culture. Such reprogramming can be effected once or repeatedly during genetic modification of recipient cells. For example, in the case of very complex genetic modifications, it may be necessary to "reprogram" recipient cells several times by the repeated introduction of donor cytoplasm to prevent senescence. The optimal frequency of such reprogramming will be determined by monitoring the doubling time of the cells in tissue culture such that the cells are reprogrammed before they become senescent.

The resultant reprogrammed genetically modified cells, which have a longer life-span as a result of reprogramming, may be used for cell and gene therapy. Moreover, these cells may be used as donor cells for nuclear transfer procedures or for the production of chimeric animals. The present methods will make it possible to produce cloned and chimeric animals having complex genetic modifications. This will be especially advantageous for the production of animal models for human diseases. Also, the present methods will be beneficial in situations wherein the expression of a desired gene product or phenotype is dependent upon the expression of different DNA sequences, or for gene research involving the interrelated effects of different genes on one another. Moreover, it is anticipated that the present methods will become very important as the interrelated effects of the expression of different genes on others becomes more understood.

Yet another application of the present invention is for alleviating the effects of aging. Just as mammalian cells have a finite life-span in tissue culture, they similarly have a finite life-span in vivo. This finite life-span is hypothesized to explain why organisms, including humans, have a normal maximum life-span, determined by the finite life-span of human somatic cells.

The present invention will alleviate the effects of aging by taking mammalian cells from an individual and altering (lengthening) the life-span of such cells by introduction of cytoplasm from an oocyte or other embryonic cell type, e.g., blastomere. The resultant rejuvenated cells may be used to produce differentiated cell types in tissue culture and these cells can then be introduced into the individual. This can be used, e.g., to rejuvenate the immune system of an individual. Such rejuvenation should be useful in the treatment of diseases thought to be of immune origin, e.g., some cancers.

Also, the subject methods may be used for the production of autologous grafts, e.g., skin grafts, which can be used in the case of tissue injury or elective surgery.

Yet another application of the present application is for treating the effects of chronologic and UV-induced aging on the skin. As skin ages, various physical changes may be manifested including discoloration, loss of elasticity, loss of radiance, and the appearance of fine lines and wrinkles. It is anticipated that such effects of aging may be alleviated or even reversed by topical application of cytoplasm-containing compositions. For example, cytoplasm from donor oocytes, e.g., bovine oocytes, optionally further including telomerase or a telomerase DNA construct, can be packaged in liposomes to facilitate internalization into skin cells upon topical application. Also, it may be advantageous to include in such compositions compounds that facilitate absorption into the skin, e.g., DMSO. These compositions may be topically applied to areas of the skin wherein the effects of aging are most pronounced, e.g., the skin around the eyes, the neck and the hands.

Still another application of the present invention is for identification of the substance or substances found in cytoplasm that induces de-differentiation. This can be effected by fractionation of cytoplasm and screening these fractions to identify those which contain substances that result in effective rejuvenation or reprogramming when transferred into recipient cells, e.g., human differentiated cell types.

Alternatively, the component(s) contained in oocyte cytoplasm responsible for reprogramming or rejuvenation can be identified by subtractive hybridization by comparing mRNA expression in early stage embryos and oocytes to that of more differentiated embryos.

With respect to such identification, it is currently unknown what component or compounds contained in embryonic cell cytoplasm are responsible for cell reprogramming or de-differentiation. In fact, it is uncertain even as to the specific nature of such component(s), e.g., whether they are nucleic acids or proteinases.

However, it is speculated by the present inventors that such component(s) may comprise nucleic acids, in particular maternal RNAs, or proteins encoded thereby. In this regard, it has been reported by different groups that very early stage embryos contain a class of RNA known as maternal RNA's that are stored in the egg very early on but which are not detected past the blastula stage. (Kontrogianni-Konstantopoulos et al, *Devel. Biol.*, 177(2):371-382 (1996).) Maternal RNA levels have been quantified for different species, i.e., rabbit, cow, pig, sheep and mouse. (Olszanska et al, J. Exp. Zool., 265(3):317-320 (1993).) With respect thereto, it has also been reported that maternal RNA in Drosophila oocyte encodes a protein that may bind to a tyrosine kinase receptor present in adjacent follicle cells that may initiate various events leading to dorsal follicle cell differentiation which act to delimit and orient the future dorsoventral axis of the embryo. (Schupbach et al, *Curr. Opin. Genet. Dev.,* 4(4): 502-507 (1994).)

Also, fractionation of oocytes has shown that mitogen-activated protein kinases are expressed at higher levels in small oocytes, suggesting that it is a maternal RNA that is stored for early embryogenesis. This is speculated to be involved in signal transduction in embryonic as well as adult cells. (Zaitsevskaya et al, *Cell Growth Differ.*, 3(11):773-782 (1992).) Still further, it has been reported that a maternal mRNA in silkworm oocytes encodes a protein that may be a structural component necessary for formation of the cellular blastoderm of the embryo, and that the association of such maternal mRNA with cortical cytoskeleton may participate in the synthesis of new cytoskeleton or related structures during blastoderm development. (Kastern et al, *Devel.*, 108(3):497-505(1990).)

Moreover, it has been reported that maternal poly(A)+ RNA molecules found in the egg of the sea urchin and amphibian oocyte are completed with U1 RNA, a co-factor in somatic nuclear pre-mRNA splicing and that such RNAs contain repeated sequences interspersed with single-copy elements. (Calzone et al, *Genes Devel.,* 2(3):305-318 (1988); Ruzdijic et al, *Development,* 101(1):107-116 (1987).)

Thus, based thereon, and the observation that cytoplasm apparently contains some component that results in cell reprogramming, it should be possible to identify compounds, likely nucleic acids and/or proteinaceous compounds which are present in the cytoplasm of oocytes and early embryos that, under appropriate conditions, provide for reprogramming or de-differentiation of desired cells. This will be effected by fractionation of cytoplasm into different fractions, e.g., based on size or isoelectric point, and ascertaining those factors which effect de-differentiation or reprogramming when transferred to differentiated cell types.

Alternatively, the factors responsible for reprogramming may be identified by subtractive or differential hybridization, essentially by identifying those mRNAs which are present in oocytes that are lost after the embryo has differentiated beyond a certain stage, e.g., past the blastula stage of development, and identifying those of which are involved in de-differentiation or reprogramming.

Therefore, the invention includes the identification of the specific cytoplasmic materials, e.g., polypeptides and/or nucleic acid sequences, which when transferred into a differentiated cell provide for de-differentiation or reprogramming. Based on what has been reported with respect to maternal RNAs, it is anticipated that the active materials responsible for de-differentiation or reprogramming may include maternal RNAs or polypeptides encoded thereby.

After such nucleic acid(s) or polypeptides have been identified and sequenced, they will be produced by recombinant methods. It is anticipated that these recombinantly produced nucleic acids or polypeptides will be sufficient to induce reprogramming or de-differentiation of desired cells.

The invention further encompasses assays wherein oocyte cytomplasm or cytoplasm from ES cells is fractionated into different fractions, e.g. based on molecular weight, isoelectric point, gel filtration, and salt precipitation, which are added into different microwells that contain one or more isolated nuclei from desired differentiated cells, e.g., mammalian, amphibian, avian, or insect cells and a screening assay conducted to identify mRNAs such as REX or OCT-4 that are released from the nuclei. For example, such mRNAs may be identified by PCR amplification and detection.

Alternatively, PCR screening assays may be conducted wherein ooplasm can be added to desired differentiated cells and assays conducted to identify what mRNAs, e.g. REX or OCT-4, are released from the cell nuclei after introduction of the oocyte cytoplasm.

The identification of such mRNAs can be identified by known methods, e.g. subtractive hybridization, differential display, and differential hyridization techniques. Essentially, these methods provide for the comparison of different populations of mRNAs in different cells, or cells at different times, and are conventionally used to identify genes that are expressed only under specific conditions or by specific types of cells.

In particular, subtractive hybridization can be effected by use of oocyte RNAs which are subtracted with RNAs obtained from normal somatic cell RNAs. Thereby, RNAs that are involved in cell reprogramming can be identified.

Additionally, the invention further includes the reconstitution of nuclei isolated from desired differentiated cells, e.g. those which are derived from differentiated cells in tissue culture, which potentially may be genetically modified by contacting such isolated nuclei with cytoplasm fractionated from oocytes, blastomeres or ES cells, and the addition of such reconstituted nuclei to cytoplasts, thereby producing a rejuvenated cell having increased proliferation potential and lifespan.

What is claimed is:

1. An in vitro method for reprogramming or increasing the life-span of a recipient cell comprising transferring part of the cytoplasm of a donor cell into an isolated recipient cell and a telomerase or a DNA construct that provides for the expression of telomerase into said recipient cell or recipient cell nucleus, wherein the donor cell is less differentiated than the recipient cell or is an undifferentiated cell, and wherein the donor cell is at or near senescence.

2. The method of claim 1, wherein said donor cell is an oocyte or an embryonic cell.

3. The method of claim 1, wherein the telomerase DNA under the control of a regulatable promoter.

4. The method of claim 1, wherein said recipient cell is a mammalian cell.

5. The method of claim 4, wherein said mammalian cell is derived from a mammal selected from the group consisting of non-human primate, human, rat, guinea pig, mouse, rabbit, dog, cat, hamster, goat, cattle, sheep, horse, bison and buffalo.

6. The method of claim 5, wherein said mammalian cell is selected from the group consisting of cardiac, lung, skin, liver, stomach, intestine, neural, muscle, bone, cartilage, immune, pancreatic, spleen, esophageal, and corneal cells.

7. The method of claim 1, wherein said recipient cell or recipient cell nucleus is genetically modified prior, concurrent or subsequent to the introduction of said cytoplasm.

8. The method of claim 7, wherein (a) said genetically modified cells comprise several genetic modifications; or (b) said genetically modified recipient cell or recipient cell nucleus comprises a recombinant DNA that encodes a desired polypeptide.

9. The method of claim 8, wherein said recombinant DNA encodes a polypeptide selected from the group consisting of a hormone, growth factor, structural polypeptide, enzyme, enzyme agonist or antagonist, antibody, antibacterial, anti-viral, anti-fungal, cytokine, clotting factor, and anti-tumor polypeptide.

10. The method of claim 1, which results in the increased life-span of a mammalian recipient cell or recipient cell nucleus.

11. The method of claim 1, wherein said donor cell is of a different species than the recipient cell.

12. The method of claim 11, wherein said donor cell is a non-human primate oocyte or embryonic cell and the recipient cell is a human somatic cell.

13. The method of claim 1, which results in the production of an embryonic stem cell.

14. A pharmaceutical composition comprising a genetically modified cell, wherein said genetically modified cell is a mammalian cell that has been reprogrammed or had its life-span increased by the introduction of part of the cytoplasm from an oocyte or embryonic donor cell of the same or different species, wherein the modified cell comprises a telomerase DNA under the control of a regulatable promoter, and wherein the donor cell is at or near senescence.

15. The pharmaceutical composition of claim 14, wherein said donor cell is an oocyte and said mammalian cell is (a) a human cell; or (b) a non-human cell.

16. The pharmaceutical composition of claim 15, wherein the genetically modified cell comprises (a) more than one genetic modification and cytoplasm from a donor oocyte; or (b) an embryonic cell is introduced into said mammalian cell at least once during the culturing of said multiply genetically modified cell in order to prevent or inhibit senescence.

17. An in vitro method for reprogramming or increasing the life-span of a cell or the nucleus thereof, the method comprising: providing a nucleus isolated from a cell; transferring part of the cytoplasm of a cytoplasm donor cell into said nucleus;

introducing a telomerase or a DNA construct that provides for the expression of telomerase into said nucleus or the cell from which said nucleus is isolated and subsequently, introducing said nucleus into a cytoplast, whereby a cell is produced that is less differentiated than the cell from which said nucleus is isolated or has an increased life-span relative to the cell from which said nucleus is isolated, and wherein the donor cell is at or near senescence.

18. The method of claim 17, wherein (a) said cytoplasm is derived from an oocyte or embryonic cell.

19. The method of claim 17, wherein the telomerase DNA under the control of a regulatable promoter.

20. The method of claim 17, wherein the cell from which said nucleus is isolated is a mammalian cell.

21. The method of claim 20, wherein said mammalian cell is obtained from a mammal selected from the group consisting of non-human primate, human, rat, guinea pig, mouse, rabbit, dog, cat, hamster, goat, cattle, sheep, horse, bison and buffalo.

22. The method of claim 17, wherein said mammalian cell is selected from the group consisting of cardiac, lung, skin, liver, stomach, intestine, neural, muscle, bone, cartilage, immune, pancreatic, spleen, esophageal, and corneal cells.

23. The method of claim 17, wherein said recipient cell or recipient cell nucleus is genetically modified prior, concurrent or subsequent to the introduction of said cytoplasm.

24. The method of claim 23, wherein said genetically modified cell comprises several genetic modifications.

25. The method of claim 24, wherein said genetically modified recipient cell or recipient cell nucleus comprises a recombinant DNA that encodes a desired polypeptide.

26. The method of claim 25, wherein said recombinant DNA encodes a polypeptide selected from the group consisting of a hormone, growth factor, structural polypeptide, enzyme, enzyme agonist or antagonist, antibody, antibacterial, anti-viral, anti-fungal, cytokine, clotting factor, and anti-tumor polypeptide.

27. The method of claim 17, which results in the increased life-span of a mammalian recipient cell or recipient cell nucleus.

28. The method of claim 17, wherein said donor cell is of a different species than the recipient cell.

29. The method of claim 28, wherein said donor cell is a non-human primate oocyte or embryonic cell and the recipient cell is a human somatic cell.

30. The method of claim 17, which results in the production of an embryonic stem cell.

31. The method of claim 5 or 21, wherein the cell is a human somatic cell.

* * * * *